United States Patent
Siewert et al.

(10) Patent No.: US 10,342,703 B2
(45) Date of Patent: Jul. 9, 2019

(54) GLAUCOMA DRAINAGE IMPLANT

(71) Applicant: UNIVERSITAET ROSTOCK, Rostock (DE)

(72) Inventors: Stefan Siewert, Rostock (DE); Frank Luderer, Rostock (DE); Wolfram Schmidt, Rostock (DE); Marian Loebler, Rostock (DE); Rudolf Guthoff, Rostock (DE); Katrin Sternberg, Dionaueschingen (DE); Klaus-Peter Schmitz, Rostock (DE)

(73) Assignee: Universitaet Rostock, Rostock (DE)

( * ) Notice: Subject to any disclaimer, the term of this patent is extended or adjusted under 35 U.S.C. 154(b) by 209 days.

(21) Appl. No.: 15/121,566

(22) PCT Filed: Feb. 23, 2015

(86) PCT No.: PCT/EP2015/053706
§ 371 (c)(1),
(2) Date: Aug. 25, 2016

(87) PCT Pub. No.: WO2015/128281
PCT Pub. Date: Sep. 3, 2015

(65) Prior Publication Data
US 2016/0367403 A1 Dec. 22, 2016

(30) Foreign Application Priority Data
Feb. 25, 2014 (DE) .................. 10 2014 102 457

(51) Int. Cl.
*A61F 9/00* (2006.01)
*A61F 9/007* (2006.01)
*D01D 5/00* (2006.01)

(52) U.S. Cl.
CPC ....... *A61F 9/00781* (2013.01); *D01D 5/0007* (2013.01); *A61F 2210/0004* (2013.01); *A61F 2240/001* (2013.01); *A61F 2250/0031* (2013.01); *A61F 2250/0067* (2013.01); *D10B 2509/00* (2013.01)

(58) Field of Classification Search
CPC .............. A61F 9/00781; A61M 27/00–27/006
See application file for complete search history.

(56) References Cited

U.S. PATENT DOCUMENTS

| 8,206,333 B2 | 6/2012 | Schmidt et al. |
| 2010/0010416 A1 | 1/2010 | Juan, Jr. et al. |

(Continued)

FOREIGN PATENT DOCUMENTS

| DE | 10 2007 004 906 A1 | 7/2008 |
| EP | 0 532 654 B1 | 7/1996 |

(Continued)

*Primary Examiner* — Benjamin Klein
(74) *Attorney, Agent, or Firm* — Muncy, Geissler, Olds & Lowe, P.C.

(57) ABSTRACT

The invention relates to an ocular implant for treating glaucoma. The problem addressed by the invention is to make it possible to drain aqueous humor from the anterior chamber of the eye into the subconjunctival or suprachoroidal space in order to lower the intraocular pressure in glaucoma cases. The device is to do away with the drawbacks of known valve mechanisms and should be economical to produce. In order to solve said problem, the glaucoma drainage implant is composed of an elongate, hollow main member in which a flow-limiting membrane is arranged in the inflow region.

13 Claims, 5 Drawing Sheets

(56) References Cited

U.S. PATENT DOCUMENTS

Figure 1:
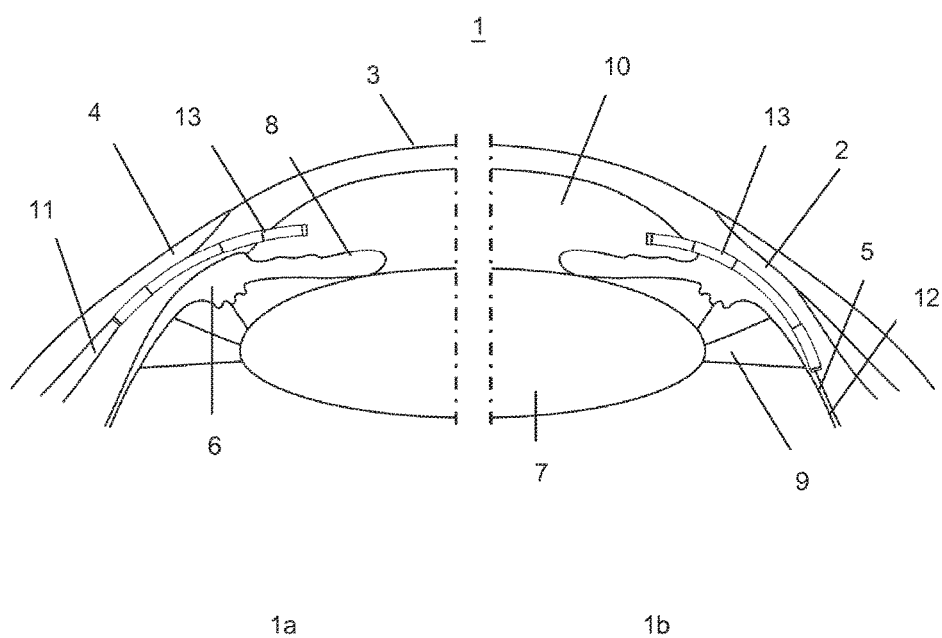

2010/0137981 A1   6/2010  Silvestrini et al.
2012/0035525 A1   2/2012  Silvestrini
2012/0089073 A1   4/2012  Cunningham, Jr.

FOREIGN PATENT DOCUMENTS

| WO | WO 98/30181 A1 | 7/1998 |
| WO | WO 99/32536 A1 | 7/1999 |
| WO | WO 2005/117780 A2 | 12/2005 |
| WO | WO 2012/071476 A2 | 5/2012 |

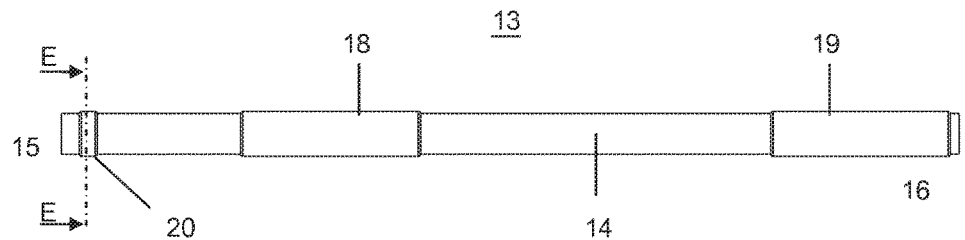
Fig. 7
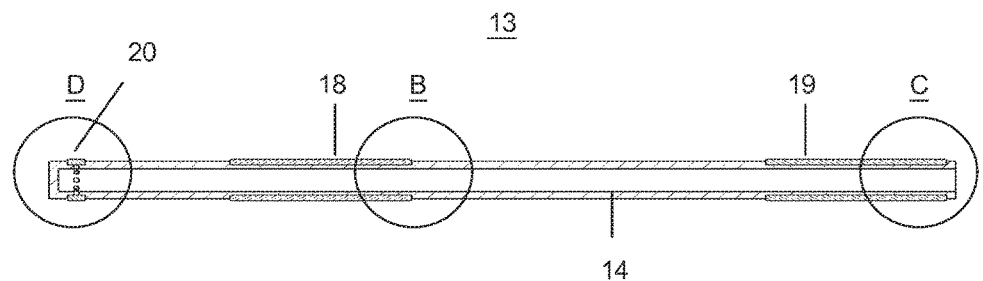
Fig. 8
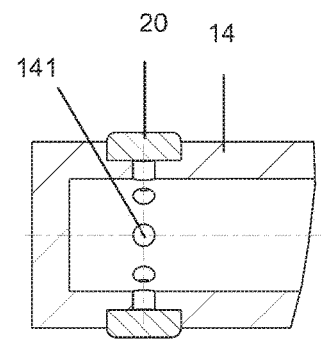 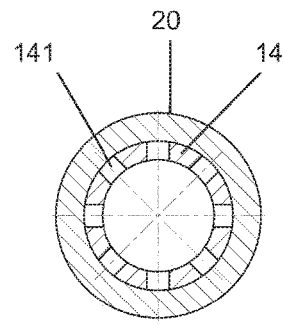
D            Schnitt E - E
Fig. 9            Fig. 10

GLAUCOMA DRAINAGE IMPLANT

CROSS REFERENCE TO RELATED APPLICATIONS

This application is a National Stage of International Application No. PCT/EP2015/053706, filed on Feb. 23, 2015, for which priority is claimed under 35 U.S.C. § 371; and this application claims priority of Application No. 10 2014 102 457.5 filed in Germany on Feb. 25, 2014 under 35 U.S.C. § 119, the entire contents of all of which are hereby incorporated by reference.

The present invention relates to an ocular implant to treat glaucoma.

Glaucoma is an optic neuropathy associated with disease progression that can lead to characteristic visual field defects up to full blindness in the affected eye. Glaucoma is the second most common cause of irreversible blindness worldwide. Permanently elevated intraocular pressure (IOP) above 21 mmHg is considered to be the main risk factor for the development of glaucoma. The intraocular pressure is regulated in the healthy eye by the circulation of aqueous humor, which is formed in the ciliary epithelium at a rate of about 2 μl/min, flows from the posterior chamber through the iris into the anterior chamber of the eye and from there, is diverted via the trabecular meshwork into the Schlemm's canal. Under physiological conditions, the intraocular pressure is approximately 15 mmHg. Intraocular pressure results from the balance between the production of aqueous humor and the aqueous humor evacuation. The aqueous humor evacuation thereby depends significantly on the outflow resistance in the trabecular meshwork. In the case of the most common form of glaucoma, primary chronic open-angle glaucoma, an increase in the outflow resistance in the trabecular meshwork leads to an increase in intraocular pressure.

Treatment methods for glaucoma generally aim to reduce intraocular pressure to a physiological level. This is primarily done with medication. In the event that only an insufficient reduction in IOP is achieved with medication, or side effects hinder the continuation of the therapy, laser procedures such as argon laser trabeculoplasty to reduce the outflow resistance in the trabecular meshwork, or microsurgical procedures such as trabeculectomy for the preparation of an additional outflow pathway for the aqueous humor under the conjunctiva are available as an alternative. Currently, trabeculectomy still represents the gold standard in the treatment of refractory glaucoma. A major disadvantage of the method is the strong dependence of therapy success on the particular surgeon. In this context, so-called glaucoma drainage implants (GDI) are a promising alternative, since the outflow resistance can be determined as early as during implant production.

A variety of commercial glaucoma drainage implants exist on the market. Among these are also implants that are minimally invasive, for example, and can be applied during cataract surgery. One known, main complication when using glaucoma drainage implants is hypotension of the eye due to excessive aqueous humor drainage. Technical solutions to this problem are described extensively in the patent literature. Therein, to avoid hypotension, e.g., complex, externally adjustable by the physician, mechatronic valve mechanisms are proposed. Taking into account economic aspects, the technical implementation hardly seems possible. Other proposed valve mechanisms for the prevention of hypotension operate according to the principle of the non-return, diaphragm, slit or reed valve and are therefore relatively easy to produce. In addition to these valve mechanisms, closing mechanisms have also been introduced which counteract hypotension in the early postoperative period and are removed at a later time, for example, by means of a laser treatment.

For example, DE 102007004906 A1 relates to a glaucoma stent, which on the one hand regulates the intraocular pressure and on the other hand prevents the flow resistance from increasing with time. A small tube with a wall surface which is formed from liquid-tight material is flowed through by the aqueous humor of the eye, wherein in the region of the wall surface at least one pressure-controlled valve is arranged.

All valve mechanisms have in common, however, the risk of functional loss with progressive implantation time, e.g., due to wear or adhesion. From clinical practice it is known that the risk of hypotension is greatest in the early postoperative period.

EP 532654 B1 (DE69120949) discloses an implant for use in the treatment of glaucoma, which comprises a flexible plate for suturing with a scleral region of the eye and a tube extending from said plate for connection to the anterior chamber. To allow for the aqueous humor to flow out in a controlled manner, in one embodiment, the drainage tube is closed with a suture or sutures until a tissue bubble has formed above the support plate. Then, the suture is removed or a dissolving suture is used. In an alternative embodiment, the drainage tube is designed as a double tube having a first lumen and a second, substantially smaller lumen. In the first lumen, a slowly dissolving plug is inserted and the second lumen is provided with a flow restrictor to allow the aqueous humor to flow gradually. Similarly, a micro-filter or a flow restrictor or valve is used as an alternative in a second outlet tube to allow for a relatively small initial current between the anterior chamber and the bubble.

US 2010137981 A1 discloses an apparatus for treating glaucoma, which is formed from an elongated, hollow body having a first portion with a braided structure and a second portion at least partially of a non-braided structure. The braided structure may be deformed during insertion, which is conducive to the retention in the eye and improves the flow of fluid from the anterior chamber.

A drainage implant for glaucoma therapy, which has flow resistance in the form of a porous, semi-permeable membrane, is described in WO 98/30181 A1. Due to the flow resistance, a low drainage effect is already to be achieved immediately upon implanting the device. After the formation of a fibrous tissue capsule around the implant, which represents the main resistance to the drainage, the flow resistance may be removed partially or completely by means of an ophthalmic laser.

US 2012/0089073 A1 describes a barrier, which initially closes at least one of potentially multiple lumens of a drainage implant for glaucoma therapy, thus counteracting hypotension. With increasing implantation time, a clearing of the initially closed lumen or of the initially closed lumens, e.g., by the decomposition of the barrier, shall occur.

US 2010/0010416 A1 introduces a drainage implant for glaucoma therapy, which allows the aqueous humor to drain from the anterior chamber of the eye into the suprachoroidal space. Various fixing structures such as projections or wings, which shall allow a mechanical fixation of the implant in the eye, are described.

An ocular implant introduced in WO 2005/117780 A2 is used to drain aqueous humor and as an interface for supplying medication to the anterior or posterior chamber of the eye. The purpose of the implant is to permit an injection or infusion, for example, of anti-glaucoma medication. For fixation of the implant in the ocular tissue, a coating is also described, which is to promote adhesion of cells.

A method for producing elongated, hollow structures is described in WO 2004/071736 A2. The method is based on phase separation, caused by the centrifugal force, of solutions or emulsions in a rotating mold.

WO 99/32536 A1 describes poly-4-hydroxybutyric acid (P4HB) as a biocompatible polymer material with controllable degradation properties.

SUMMARY OF THE INVENTION

The present invention has the object of facilitating aqueous humor drainage from the anterior chamber of the eye, for example, into the subconjunctival or the suprachoroidal space, in order to reduce intraocular pressure in cases of glaucoma. The aim of the device is to circumvent the drawbacks of known valve mechanisms, and should be economical to produce.

According to the invention, the object is achieved by the main features of the claims. For this purpose, the glaucoma drainage implant is formed of an elongated, hollow base body in which a flow-limiting membrane is arranged in the inflow region.

For an essential embodiment, distributed around the periphery of a front, closed end of the base body, holes are arranged, which are covered by the overlying membrane.

For a further embodiment, the membrane is made of biodegradable, semi-permeable material. This material can be a polymeric material, such as poly (4-hydroxybutyric acid).

For a further embodiment, the membrane has decreasing flow resistance with increasing implantation time.

The membrane made of a biostable, semi-permeable material is a further embodiment.

For an inventive glaucoma drainage implant in another embodiment, a fixing element is arranged on approximately one-third of the tubular body as seen from a front end, which serves for the fixation of the implant in the tissue.

In order to avoid the formation of a fibrous tissue capsule, a local drug delivery system is arranged at a rear end of the base body.

Local grooves in the wall surface of the base body are used to hold the diaphragm, the fixing element and the local drug delivery system.

To produce the membrane, the fixing element and the local drug delivery system, a manufacturing process in the form of electrospinning is used.

The inflow region of the implant is implanted in the anterior chamber of the eye and the outflow region of the implant is implanted into the suprachoroidal or subconjunctival space.

The glaucoma drainage implant according to the invention with a temporarily increased flow resistance represents a promising alternative to mechanical valve mechanisms.

EMBODIMENT OF THE INVENTION

The invention is further illustrated with reference to embodiments.

The drawings show

Figure 2:
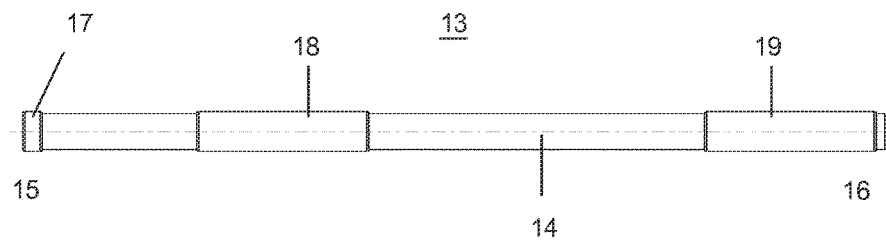
Figure 3:
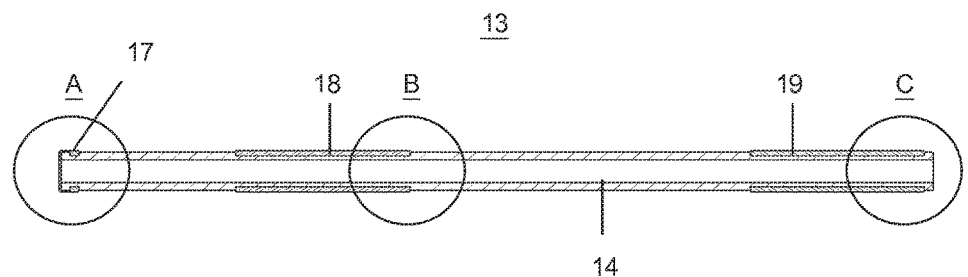
Figures 4, 5, 6:
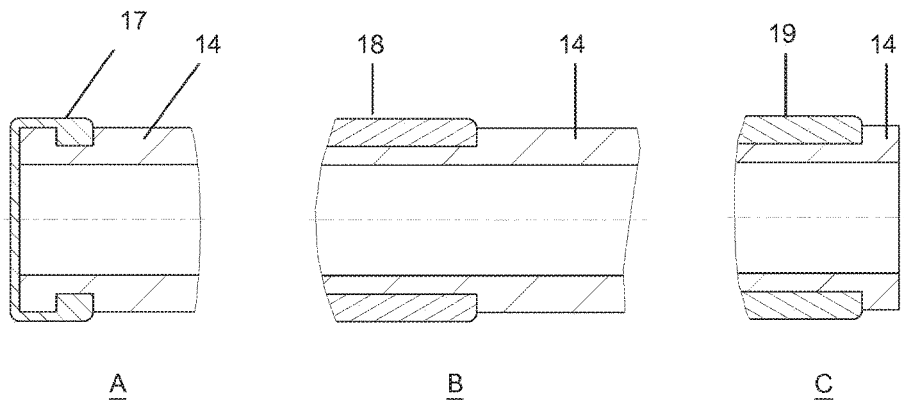
Figure 11:
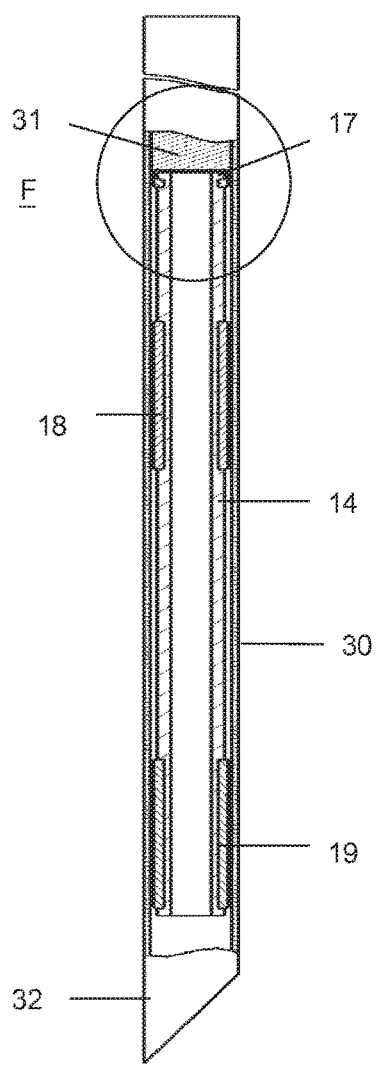
Figure 12:
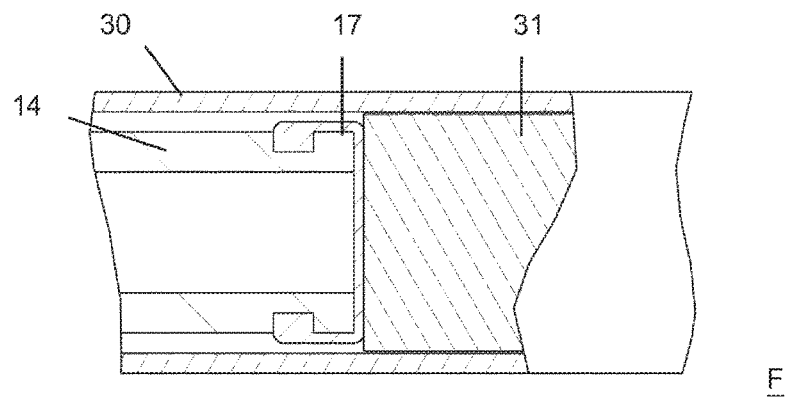
Figure 13:
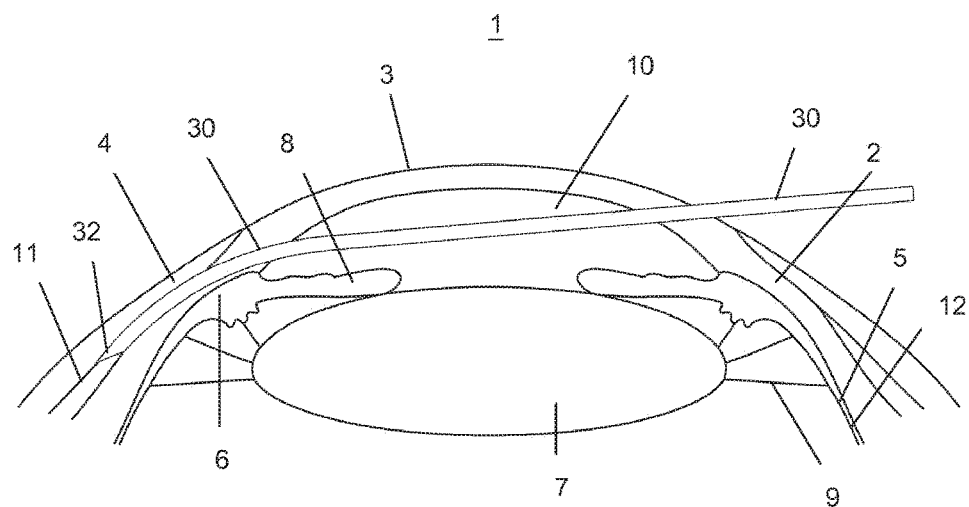
Figure 13:
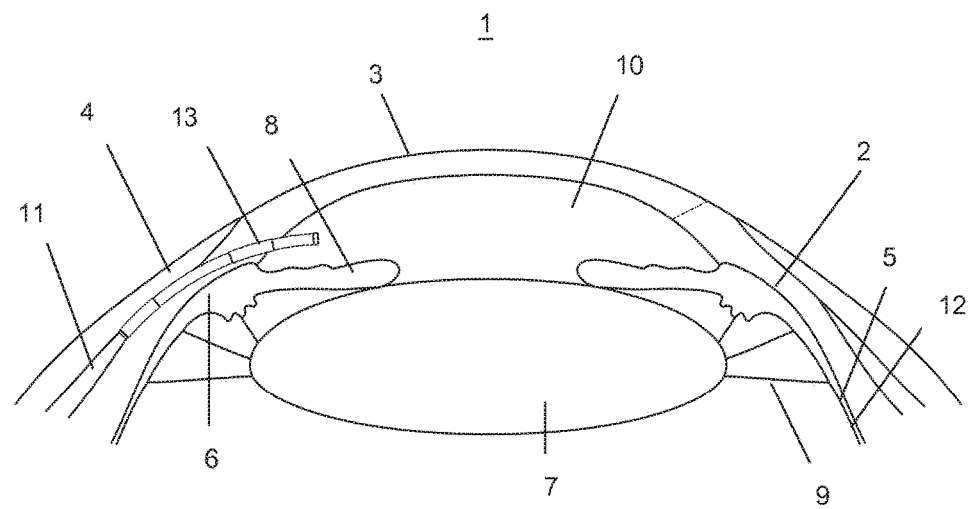

FIG. 1 a schematic representation of the eye with two possible drainages from the anterior chamber of the eye with
  FIG. 1a a drainage in the subconjunctival space or
  FIG. 1b a drainage in the suprachoroidal space, FIG. 2 a first embodiment of the glaucoma drainage implant according to the invention,
FIG. 3 a sectional view of FIG. 2,
FIG. 4 a detailed view A of FIG. 3,
FIG. 5 a detailed view B of FIG. 3,
FIG. 6 a detailed view C of FIG. 3,
FIG. 7 a second embodiment of the glaucoma drainage implant according to the invention,
FIG. 8 a sectional view of FIG. 7,
FIG. 9 a detailed view D of FIG. 8,
FIG. 10 a section E-E of FIG. 7,
FIG. 11 an injector with included glaucoma drainage implant,
FIG. 12 a detailed view F of FIG. 11 and
FIG. 13 a representation of a minimally invasive implant with the schematic phases a and b.

FIG. 1 schematically shows the eye. The structure of the eye 1 described herein is limited to the essential parts relevant for the invention (which are identical for the FIGS. 1a and 1b) with the sclera 2, the cornea 3, the conjunctiva 4, the choroid 5, the ciliary body 6, the lens 7, the iris 8 and the zonular fibers 9. Further, two possible arrangements are for the reduction of intraocular pressure in glaucoma with a glaucoma drainage implant 13 (short: implant) from the anterior chamber 10 of the eye into the subconjunctival space 11 between the conjunctiva 4 and the sclera 2 (FIG. 1a, left), and the drainage from the anterior chamber 10 of the eye into the suprachoroidal space 12 between the sclera 2 and the choroid 5 (FIG. 1b, right).

Various embodiments of the glaucoma drainage implant 13 are shown in FIGS. 2 to 10. It is made of a flexible, elongated, for example, cylindrical base body 14, which is hollow inside and is divided into several sections and has a front end 15 (inlet end) and a rear end 16 (outlet end).

A first embodiment of the glaucoma drainage implant 13 according to the invention is shown in FIGS. 2 to 6. A first section A is located at the front end 15. Here, a flow-limiting, preferably biodegradable, semi-permeable membrane 17 is arranged in the inflow region of the implant 13 for the purpose of preventing hypotension, which covers the axial inflow lumen. In the detailed view A in FIG. 4, this is shown more clearly. The flow-limiting membrane 17 is designed for maximum aqueous humor drainage of, e.g., 2 µl/min at a pressure difference of, e.g., 15 mmHg (subconjunctival space) or e.g., 2 mmHg (suprachoroidal space) at the time of implantation. Weeks after implantation, a fibrous tissue capsule has usually formed around the implant 13 in the outflow region that then represents the primary resistance to the drainage. Therefore, with increasing implantation time, a degradation of the flow-limiting membrane 17 can take place, whereby the flow resistance of the implant 13 gradually decreases. By balancing the increasing flow resistance of the fibrous tissue capsule with the diminishing flow resistance of the implant 13, an approximately constant aqueous humor drainage of e.g., 2 µl/min, and thus a reduction in intraocular pressure, can be ensured.

The second section B is located on the glaucoma drainage implant 13 on approximately one third of the tubular base body 14 as seen from the front end 15. In this case, this is an optional fixing element 18, which is used for optimum healing and fixation of the implant 13 within the tissue. The fixing element 18 is preferably arranged circularly around the entire circumference of the implant 13. Alternatively, a distribution of a fixing element 18 having one, two or more elements is possible in individual sections over the circumference of the implant 13.

The third section C is arranged at the rear end 16 and is a local drug delivery system 19 (LDD) coupled with the glaucoma drainage implant 13 to avoid the formation of a fibrous tissue capsule. The local drug delivery system 19 is preferably arranged circularly around the entire circumference of the implant 13. Alternatively, a distribution of a local drug delivery system 19 having one, two or more elements is possible in individual sections over the circumference of the implant 13.

FIGS. 7 to 10 illustrate the second embodiment of the glaucoma drainage implant 13 according to the invention. Here also, a flow-limiting, preferably biodegradable, semi-permeable membrane 20 is used in the inflow region of the implant 13. FIG. 9 shows the section D as a detailed view, which substantially corresponds to the section A of FIG. 4. The base body 14 of the glaucoma drainage implant 13 is closed at its front end 15 as opposed to FIG. 4. The membrane 20 is directly incorporated in the base body 14, spaced from the front end 15. FIG. 10 shows a section E-E through the implant 13 with its base body 14 and the membrane 20. In order to limit the flow of the aqueous humor, holes 141 that are covered by the overlying membrane 20 are arranged as radial inflow openings that are distributed around the periphery of the base body 14. As a result, even after the complete degradation of the membrane 20, flow resistance required for the prevention of hypotension can be maintained.

Alternatively, a biostable, that is, not biodegradable, design of the flow-limiting, semi-permeable membrane is conceivable for both the first and the second embodiment of the glaucoma drainage implant 13. This embodiment, however, should preferably be used in combination with the local drug delivery system 19 (LDD), coupled to the glaucoma drainage implant 13, to avoid the formation of a fibrous tissue capsule.

As a method for the preparation for flow-limiting membranes 17 and 20, electrospinning is preferably used. This method enables direct spinning of the implant base body 14 and an exact adjustment of the flow resistance by varying different process parameters. With this method, both the membrane 17 covering the axial inflow lumen as well as the membrane 20 covering the additionally created radial inflow openings can be manufactured. As a material for the flow-limiting, biodegradable membranes 17 and 20, for example, the polymer material poly (4-hydroxybutyric acid) is used.

The electrospinning method is potentially suitable for the production of other components of the implant, such as the local drug delivery system 19 or the fixing element 18. Here, any polymer materials can be spun also in combination with the appropriate medication. To inhibit fibrosis, the drug mitomycin C known from the field of trabeculectomy is of interest for the local drug delivery system 19. The local promotion of cell adhesion and the resulting optimum healing in the tissue may be provided for the fixing element 18, for example, via RGD integrin interaction. The implant base body 14 is preferably made of an elastomer, for example, silicone or polyurethane. The shape of the implant 13 is preferably cylindrical, so that a minimally invasive implantation with the aid of an injector 30 is possible. The injector 30 containing a glaucoma drainage implant 13 is shown in FIGS. 11 and 12. For this embodiment, the glaucoma drainage implant 13 is prepared for implantation with the flexible, preferably cylindrical base body 14, the flow-limiting, preferably biodegradable, semi-permeable membrane 17, the fixing element 18 and the local drug delivery system 19. The flexible injector 30 is designed in this embodiment, at its distal end, for example, with a sharp tip 32 to facilitate penetration of the ocular tissue. At its proximal end, a plunger 31 is introduced into the injector 30, by means of which the glaucoma drainage implant 13 is advanced to the desired implantation site. The glaucoma drainage implant 13 is loaded into the injector 30, wherein the membrane 17 or 20 sits opposite the tip 32 of the injector 30. The injector 30 is sealed with a plunger 31, which is used at the same time to propel the glaucoma drainage implant 13 into the interior of the eye. FIG. 12 shows a detailed view F of FIG. 11, in which the position of the glaucoma drainage implant 13 in front of the plunger 31 is illustrated.

In order to obtain a smooth outer surface of the base body 14 and to therefore promote a minimally invasive implantation, the functional elements flow-limiting membrane 17 and 20, local drug designation delivery system 19 and fixing element 18 are preferably integrated in corresponding local grooves in the wall surface of the base body 14.

A possible, minimally invasive implantation procedure is illustrated in FIG. 13, wherein the individual drawings A and B schematically show various phases of implantation. FIG. 13a shows the eye 1 during the procedure, that is, the time of implantation. For this purpose, the injector 30 with the glaucoma drainage implant 13 is advanced through a small incision of the cornea 3 up to the implantation site, in this case, the subconjunctival space. With the aid of a plunger 31, the implant 13 is released from the injector 30. FIG. 13b shows the schematic arrangement of the liberated glaucoma drainage implant 13 at the implantation site.

REFERENCE NUMERALS 1 eye
2 sclera
3 cornea
4 conjunctiva
5 choroid
6 ciliary body
7 lens
8 iris
9 zonular fibers
10 anterior chamber
11 subconjunctival space
12 suprachoroidal space
13 glaucoma drainage implant
14 elongated hollow base body
  141 holes
15 front end (inlet end)
16 rear end (outlet end)
17 membrane
18 fixing element
19 local drug delivery system
20 membrane
30 injector
31 plunger
32 tip

The invention claimed is:
1. A glaucoma drainage implant for implantation in an eye, the implant comprising:
  an elongated, hollow base body having a front end and a rear end, the front end having a wall such that the front end is closed and the rear end being open;
  holes distributed around an outer circumference of the base body at a position that is adjacent the wall of the front end, the holes forming an inflow region of the base body;

a flow-limiting membrane overlying the holes, such that the membrane covers the inflow region of the base body;

a local drug delivery system arranged adjacent the rear end of the base body;

a fixing element arranged between the membrane and the local drug delivery system; and local grooves recessed in an outer surface of the base body, a first one of the local grooves for accommodating the membrane, a second one of the local grooves for accommodating the fixing element and a third one of the local grooves for accommodating the local drug delivery system.

2. Glaucoma drainage implant according to claim 1, wherein, the fixing element is arranged to overlay the base body at a position that is one-third of a length of the base body measured from the front end, wherein the fixing element fixes the implant in tissue of the eye.

3. Glaucoma drainage implant according to claim 1, wherein, the fixing element is produced by electrospinning.

4. Glaucoma drainage implant according to claim 1, wherein the local drug delivery system is arranged at the rear end of the base body, the local drug delivery system including medication therein that deters formation of a fibrous tissue capsule when the implant is implanted in the eye.

5. Glaucoma drainage implant according to claim 1, wherein, the local drug delivery system is produced by electrospinning.

6. Glaucoma drainage implant according to claim 1, wherein the membrane is made from biodegradable, semi-permeable material.

7. Glaucoma drainage implant according to claim 1, wherein the membrane is made of a polymeric material.

8. Glaucoma drainage implant according to claim 1, wherein the membrane is made of poly (4-hydroxybutyric acid).

9. Glaucoma drainage implant according to claim 6, wherein, after the implant is implanted in the eye, the membrane begins to degrade, such that the membrane has a decreasing flow resistance with an increasing implantation time.

10. Glaucoma drainage implant according to claim 1, wherein the membrane is made of a biostable, semi-permeable material.

11. Glaucoma drainage implant according to claim 1, wherein, the membrane is produced by electrospinning.

12. Glaucoma drainage implant according to claim 1, wherein the fixing element and the local drug delivery system are each formed of a polymer and the base body is formed of an elastomer.

13. Glaucoma drainage implant according to claim 1, wherein the fixing element and the local drug delivery system are each ring-shaped such that they are each arranged circularly around a circumference of the base body.

\* \* \* \* \*

UNITED STATES PATENT AND TRADEMARK OFFICE
CERTIFICATE OF CORRECTION

PATENT NO. : 10,342,703 B2
APPLICATION NO. : 15/121566
DATED : July 9, 2019
INVENTOR(S) : Siewert et al.

Page 1 of 1

It is certified that error appears in the above-identified patent and that said Letters Patent is hereby corrected as shown below:

On the Title Page

Shows:
(72) Inventors: Stefan Siewert, Rostock (DE); Frank Luderer, Rostock (DE); Wolfram Schmidt, Rostock (DE); Marian Loebler, Rostock (DE); Rudolf Guthoff, Rostock (DE); Katrin Sternberg, Dionaueschingen (DE); Klaus-Peter Schmitz, Rostock (DE)

Should show:
(72) Inventors: Stefan Siewert, Rostock (DE); Frank Luderer, Rostock (DE); Wolfram Schmidt, Rostock (DE); Marian Loebler, Rostock (DE); Rudolf Guthoff, Rostock (DE); Katrin Sternberg, Donaueschingen (DE); Klaus-Peter Schmitz, Rostock (DE)

Signed and Sealed this
Fifteenth Day of October, 2019

Andrei Iancu
*Director of the United States Patent and Trademark Office*